(12) United States Patent
Rizoiu et al.

(10) Patent No.: US 6,616,447 B1
(45) Date of Patent: Sep. 9, 2003

(54) DEVICE FOR DENTAL CARE AND WHITENING

(75) Inventors: Ioana M. Rizoiu, San Clemente, CA (US); Andrew I. Kimmel, San Clemente, CA (US)

(73) Assignee: BioLase Technology, Inc., San Clemente, CA (US)

( * ) Notice: Subject to any disclaimer, the term of this patent is extended or adjusted under 35 U.S.C. 154(b) by 0 days.

(21) Appl. No.: 09/991,533

(22) Filed: Nov. 15, 2001

Related U.S. Application Data
(60) Provisional application No. 60/249,015, filed on Nov. 15, 2000.

(51) Int. Cl.[7] .................................................. A61C 9/00
(52) U.S. Cl. ........................................ 433/29; 433/216
(58) Field of Search .......................... 433/29, 37, 215, 433/216

(56) References Cited

U.S. PATENT DOCUMENTS

| | | | | |
|---|---|---|---|---|
| 4,553,936 A | * | 11/1985 | Wang | 433/37 |
| 4,867,682 A | * | 9/1989 | Hammesfahr et al. | 433/37 |
| 5,316,473 A | * | 5/1994 | Hare | 433/29 |
| 5,487,662 A | * | 1/1996 | Kipke et al. | 433/37 |
| 5,718,577 A | * | 2/1998 | Oxman et al. | 433/37 |
| 6,077,073 A | * | 6/2000 | Jacob | 433/29 |
| 6,162,055 A | * | 12/2000 | Montgomery et al. | 433/216 |
| 6,391,283 B1 | * | 5/2002 | Jensen et al. | 424/49 |
| 6,416,319 B1 | * | 7/2002 | Cipolla | 433/29 |

* cited by examiner

*Primary Examiner*—Ralph A. Lewis
(74) *Attorney, Agent, or Firm*—Stout, Uxa, Buyan & Mullins LLP

(57) ABSTRACT

A dental device for exposing teeth to electromagnetic radiation includes a carrier and at least one source of electromagnetic radiation attached to the carrier and oriented so that the electromagnetic radiation is emitted from the source to a surface of a tooth. The dental device may also include a power source internally or externally disposed with respect to the carrier, and may include a circuit for controlling radiation emitted from the source. The dental device may be used for whitening teeth, and dental hygiene in general. Related methods are also disclosed.

28 Claims, 4 Drawing Sheets

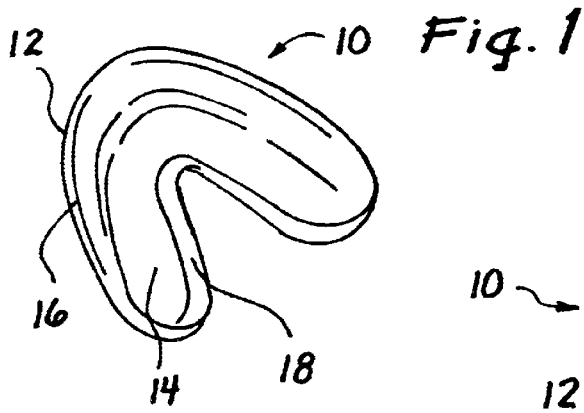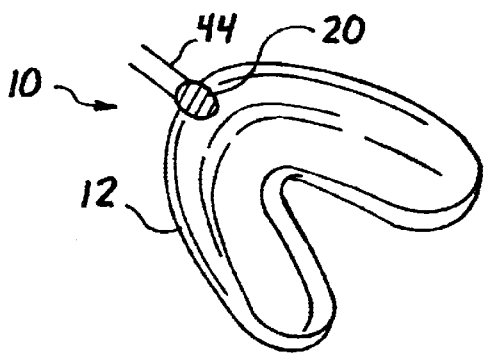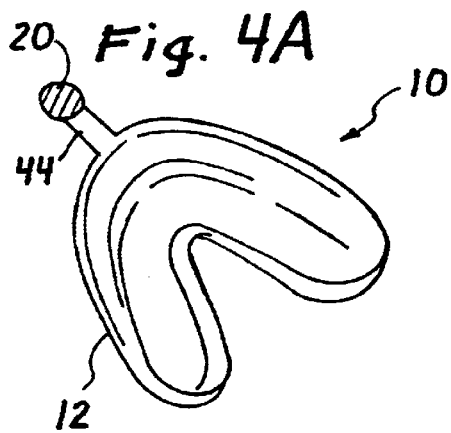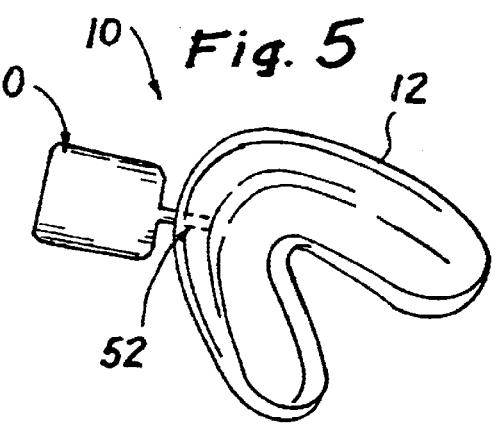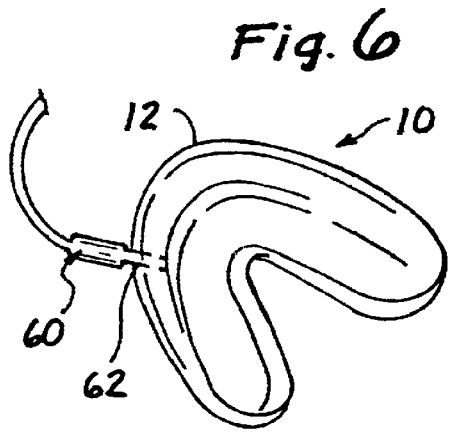

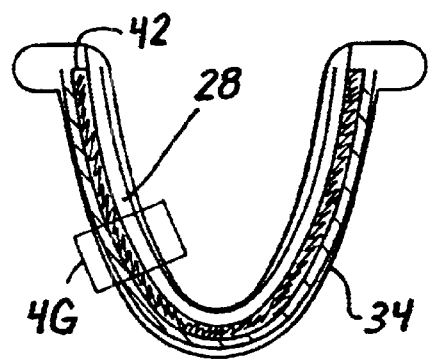
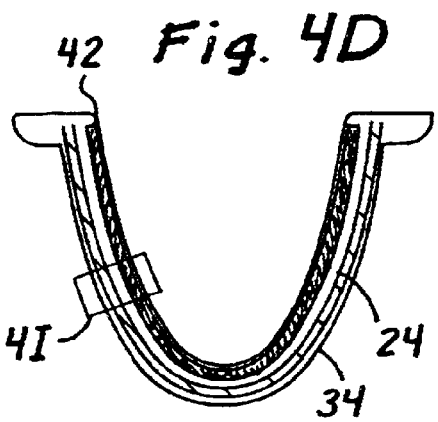
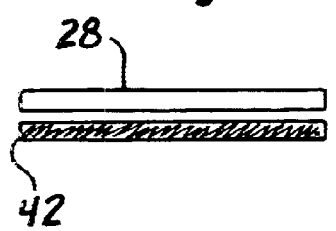
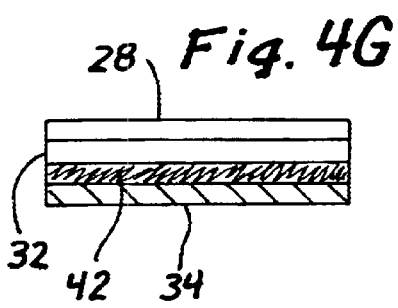
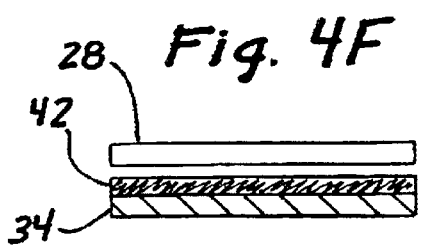
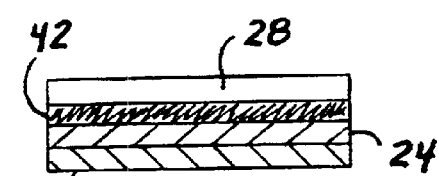
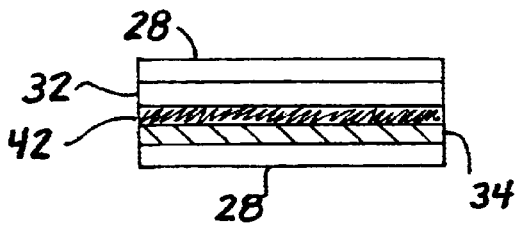

DEVICE FOR DENTAL CARE AND WHITENING

CROSS-REFERENCE TO RELATED APPLICATIONS

This application claims the benefit of U.S. Provisional Application No. 60/249,015, entitled DEVICE FOR DENTAL CARE AND WHITENING, and filed Nov. 15, 2000, the entire contents of which are hereby incorporated by reference.

BACKGROUND OF THE INVENTION

1. Field of the Invention

This application relates to dental hygiene, and in particular, relates to devices and methods for exposing teeth to electromagnetic radiation.

2. Description of Related Art

Dental hygiene is important for dental health and for personal appearance. People often desire to have whiter or cleaner teeth. A number of different devices and methods are known in the art for whitening and cleaning teeth. Several methods utilize a whitening agent, such as peroxide, alone or in combination with other agents, to attempt to whiten teeth. In certain processes, the whitening agent is applied to teeth by brushing the teeth with a dentifrice, such as a paste, gel, liquid, cream, or powder, containing the whitening agent. Other methods employ dental trays or dental stints that have received an application of a whitening agent. In such methods, the dental tray is pressed onto the teeth, and the whitening agent is permitted to bathe or coat the teeth (e.g., see U.S. Pat. No. Re. 34,196, entitled METHOD AND MATERIAL FOR BRIGHTENING TEETH). Another method employs a dental tray having a heating element wire disposed within the tray (e.g., see U.S. Pat. No. 6,102,705, entitled HEATED DENTAL TRAY). In that method, a whitening agent is applied to a dental tray having a heating element wire, and the tray is pressed onto the teeth of a person. Current then passes through the wire and heats the teeth. In yet another method, lasers are used to enhance the effects of whitening agents (e.g., see U.S. Pat. No. 6,254,388, entitled METHODS FOR WHITENING TEETH; and U.S. Pat. No. 6,155,832, entitled METHODS AND APPARATUS FOR WHITENING TEETH). In U.S. Pat. No. 6,254,388, argon laser energy is manually directed over a person's tooth. The soft tissues of the mouth, such as the gums, is protected by rubber dams or adhesive wax. In U.S. Pat. No. 6,155,832, laser light is manually directed and used to activate whitening agents provided on dental tape.

Currently known devices and methods may suffer from the problem that the effectiveness of the whitening agent is not maximized, or that the use of lasers requires manual guidance over each tooth in order to achieve the desired whitening. Accordingly, there remains an unmet need for a device that provides substantial whitening or cleaning of teeth and eliminates the need for manually guiding an energy source over the teeth.

SUMMARY OF THE INVENTION

The present invention provides a device and methods for exposing teeth to electromagnetic radiation. The devices and methods improve dental hygiene, and may enhance the cosmetic appearance of teeth.

The dental device of the invention broadly includes a carrier, and at least one electromagnetic radiation source. The carrier may include, but is not limited to, dental trays, dental bands, and/or dental tape. The electromagnetic radiation source may be a light source. The energy emitted from the electromagnetic radiation source may have one or more wavelengths between the ultraviolet light spectrum and the infra-red light spectrum. The radiation may activate hygienic or cleaning agents provided in dentifrices.

The dental device of the invention may also include a power supply to power the electromagnetic radiation source, and/or may include a circuit for controlling the electromagnetic radiation source(s).

A dental device for exposing teeth to electromagnetic radiation may include a carrier to be applied to at least one tooth; and one or more light sources attached to the carrier and oriented so electromagnetic radiation is emitted from the light source or sources toward a tooth surface.

The carrier of the foregoing device may be a dental tray, a dental band, or dental tape. The light source may be a light emitting diode, an optical fiber, or an electrochemiluminescent material. The optical fibers may be provided as an optical fiber panel.

A dental device for exposing teeth to electromagnetic radiation may also comprise a dental tray structured to fit over the teeth of a subject; and a plurality of optical fibers to provide electromagnetic radiation to at least one tooth. The optical fibers can be disposed on the dental tray so that the electromagnetic radiation is directed to at least one tooth. The optical fibers may define an optical fiber panel.

The foregoing devices may also include a power source in communication with the light source. The power source would provide power to the light source so that the light may be emitted from the light source. The foregoing devices may also include one or more circuits for controlling the electromagnetic radiation emitted from the light source. In addition, the foregoing devices may include one or more panels, including a reflective panel, a diffuser panel, and/or one or more transparent panels. The panels may contribute to the structure of the light source arrays, and may enhance or improve the effects of the electromagnetic radiation. The reflective panel may be positioned between the light source and the carrier. The diffuser panel may be positioned over the light source so that light emitted from the light source passes through the diffuser. The transparent panel may be provided over the light source, and/or may be provided between the light source and the carrier. The foregoing devices may also include an optical fiber bundle operably connected with the light source so that optical energy may be transmitted from the optical fiber bundle to the light source.

A method for exposing teeth to electromagnetic radiation comprises the steps of: (a) providing a dental device, which comprises a carrier and a plurality of optical fibers disposed on or in the carrier; (b) applying a dentifrice containing an agent having cleaning properties, the cleaning activity of the agent activated by electromagnetic radiation provided by the optical fibers to the dental device; (c) applying the dental device to a subject's teeth; and (d) activating a power source so that electromagnetic radiation is emitted from the optical fibers toward the dentifrice and the subject's teeth. The carrier used in the foregoing may be a dental tray.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

BRIEF DESCRIPTION OF THE DRAWINGS

FIG. 1 is a perspective view of a dental device in accordance with the present invention.

FIG. 4A is similar to FIG. 1 depicting a perspective view of the device of the invention having a fiber optic bundle and an internal electromagnetic radiation source.

FIG. 4B is similar to FIG. 4A illustrating an embodiment of the device of the invention in which the electromagnetic radiation source is externally located.

FIG. 4C is a top plan view of the device of FIG. 4A depicting a transparent panel, a diffuser, an optical fiber panel, and a reflective panel.

FIG. 4D is similar to FIG. 4C but depicting a transparent panel, an optical fiber panel, a light source panel and a reflective panel.

FIG. 4E is a portion of a top plan view of the device of the invention depicting a transparent panel and an optical fiber panel.

FIG. 4F is a portion of a top plan view of the device of the invention depicting a transparent panel, an optical fiber panel, and a reflective panel.

FIG. 4G is a portion along the box 4G of FIG. 4C depicting a transparent panel, a diffuser panel, an optical fiber panel, and a reflective panel.

FIG. 4H is a portion of a top plan view of the device of the invention depicting two transparent panels, a diffuser panel, an optical fiber panel, and a reflective panel.

FIG. 4I is a portion along the box 4I of FIG. 4D depicting a transparent panel, an optical fiber panel, a light source panel, and a reflective panel.

FIG. 5 is a perspective view of the device of the invention having a dentifrice cartridge connected to the device.

FIG. 6 is a perspective view of the device of the invention having an aspirator connected to the device.

DETAILED DESCRIPTION OF THE PRESENTLY PREFERRED EMBODIMENTS

Figure 1A:
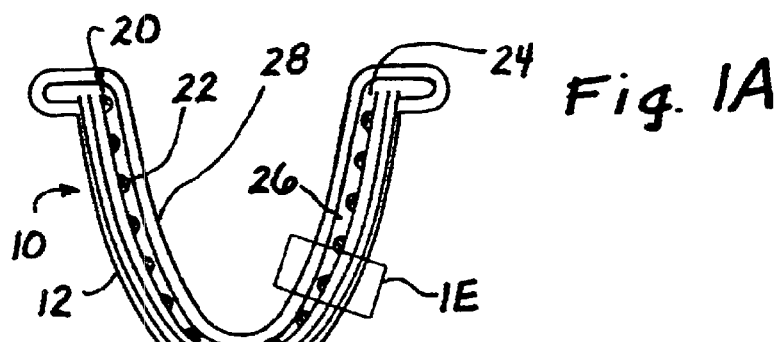
FIG. 1A is a top plan view of the device illustrated in FIG. 1.

Although the disclosure herein refers to the use of a dental device for whitening teeth, the device is not limited to such uses and may be used for any dental hygienic purpose that may benefit from the application of electromagnetic energy.

The device of the invention generally includes a carrier, such as a dental tray, a dental band, or a dental tape, or other similar device, and one or more electromagnetic radiation sources that can emit electromagnetic radiation toward the surface of one or more teeth. The electromagnetic radiation, especially when combined with a dentifrice, such as a paste, gel, cream, or powder, may improve dental hygiene, for example by whitening teeth, reducing bacteria, inhibiting caries, preventing tooth demineralization, etching tooth enamel or dentin, and other similar methods.

The device of the invention may also be provided with a circuit, and/or microprocessor, for controlling the electromagnetic radiation sources. The device may also include one or more power supplies for providing energy to the electromagnetic radiation sources.

As used herein, electromagnetic radiation or electromagnetic energy refers to monochromatic or polychromatic radiation or energy. In a preferred embociment, electromagnetic radiation refers to light radiation or light energy. The electromagnetic radiation preferably increases the reaction rate of photosensitive agents, such as teeth whitening agents. In accordance with one aspect of the present invention, the electromagnetic radiation may be substantially free from ultraviolet radiation. In addition, the wavelengths of the electromagnetic radiation may be provided between approximately 300 and 990 nanometers, or up to about 1 $\mu$m. Any suitable means may be used to generate the electromagnetic radiation. For example, a semiconductor laser may be implemented to generate monochromatic electromagnetic radiation, or a light emitting diode (LED) may be configured to emit polychromatic electromagnetic radiation. A non-limiting example of a laser source may comprise a Nd:YAG laser, although various other lasers having various wavelengths in the UV, visible and IR spectrum, for example, may be implemented individually or in combinations.

Referring more particularly to the illustrated embodiments, FIG. 1 provides a perspective view of a dental device 10. As illustrated in FIG. 1, dental device 10 comprises a dental tray 12 configured to fit over a person's teeth. For example, dental tray 12, as shown, may fit over a person's upper teeth. Dental trays are well-known in the art. Dental tray 12 may be generic or custom designed. The dental tray will fit within a person's mouth, and may cover all of the upper or lower teeth or a portion thereof. In certain embodiments, one dental tray may fit over both the upper and lower teeth, such as a mouth guard typically worn by athletes. In the illustrated embodiment, dental tray 12 includes a tooth bed 14 positioned between an outer sidewall 16 and an inner sidewall 18. Teeth are intended to be placed into tooth bed 14. Outer sidewall 16 will accordingly be disposed between the outer surface of the teeth and a subject's cheeks, and inner sidewall 18 will be disposed between the inner surface of the subject's teeth and the mouth cavity.

Dental trays may be manufactured from any suitable material including rubbers and plastics, including, but not limited to polyethylenes, polypropylenes, and ethyl vinyl acetates. Dental trays may be manufactured in any conventional method. For example, a custom dental tray may be made by making an impression of a subject's teeth, and may be vacuum or thermoformed over the impression. Dental trays designed to simultaneously fit over the upper and lower teeth may include through holes to provide an air passage so that the wearer of the dental tray may breathe.

As shown in FIG. 1A, dental tray 12 includes an electromagnetic radiation source 20, such as LEDs 22. LEDs 22 are perimetrically disposed along the interior of the outer sidewall of the dental tray so that energy emitted from the LEDs will be emitted toward the outer surface of a subject's teeth. In the illustrated embodiment, LEDs 22 are attached to light source panel 24. Thus, LEDs 22 are provided as a strip or array of LEDs embedded, molded, mounted, potted, or otherwise bonded on or within the tray. The LED array may include side-mounted LEDs (FIG. 2), surface-mounted LEDs (FIG. 3), or a combination of surface- and side-mounted LEDs. An example of one suitable LED is the publicly available 1005 Series of LEDs from Marktech Optoelectronics (Latham, N.Y., USA).

Figure 1B:
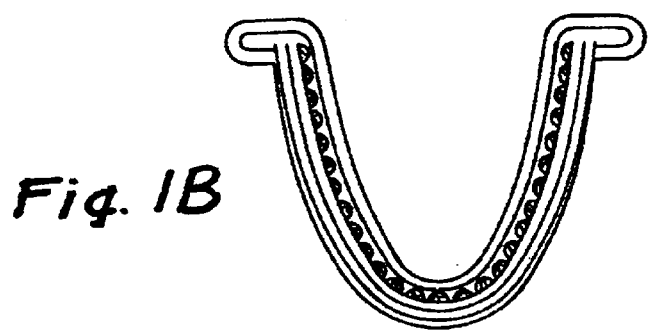
FIG. 1B is a top plan view of the device illustrated in FIG. 1, showing light emitting diodes spaced relatively close together.
Figure 1C:
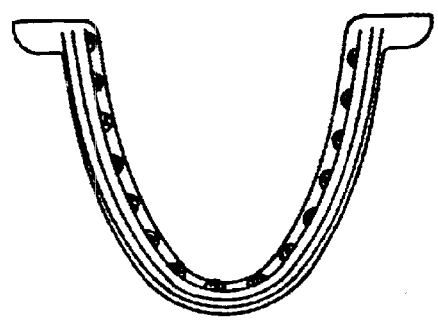
FIG. 1C is a top plan view of the device illustrated in FIG. 1 without a transparent panel covering light emitting diodes.
Figure 1D:
FIG. 1D is a portion of a top plan view of the device illustrated in FIG. 1 showing a transparent panel, light emitting diodes, and a light source panel.
Figure 1E:
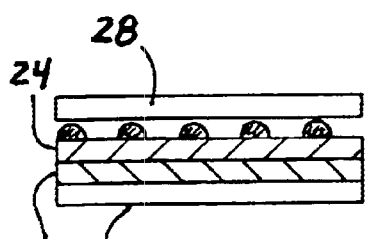
FIG. 1E is a portion along box 1E of FIG. 1A showing a transparent panel, light emitting diodes, a light source panel, and a reflective panel.
Figure 1F:
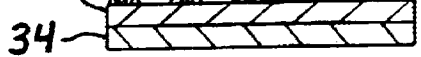
FIG. 1F is similar to FIG. 1E but showing two transparent panels, light emitting diodes, a light source panel, and a reflective panel.
Figure 1G:
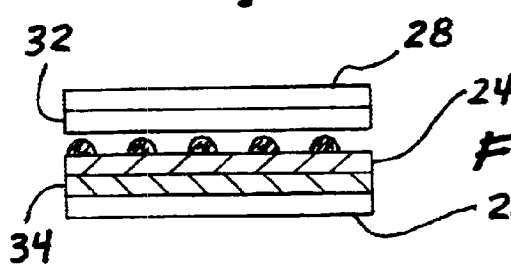
FIG. 1G is similar to FIG. 1F showing a diffuser panel disposed between one transparent panel and the light emitting diodes.
Figure 2:
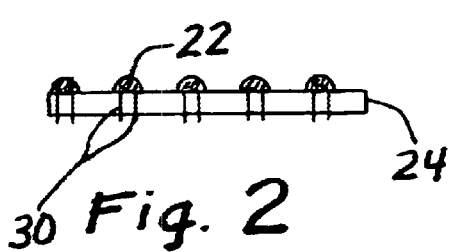
FIG. 2 is similar to FIG. 1D without the transparent panel, and showing the use of side mounted contacts.
Figure 3:
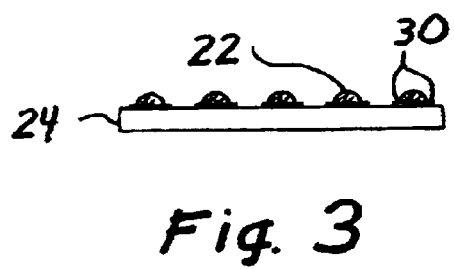
FIG. 3 is similar to FIG. 2 showing surface mounted contacts.

Although LEDs are illustrated as the electromagnetic radiation source in FIGS. 1–3, other electromagnetic radiation sources may also be used. Examples of other electromagnetic radiation sources include, but are not limited to, heat emitting elements, chips from and LED, lasers or laser diodes, arc lamps, incandescent lamps, halogen lamps, neon lamps, and/or fluorescent sources. The electromagnetic radiation sources may emit electromagnetic radiation from ultraviolet to visible to infra-red light. In one embodiment, infra-red spectral energy may be preferred.

LEDs 22 may be covered by a relatively clear or transparent material. The transparent material may be provided as a transparent panel 28 disposed between LEDs 22 and the outer surface of the teeth, as shown in FIG. 1A. However, the transparent material may also be the surface of the dental tray, and not comprise a separate transparent panel, as shown in FIG. 1C.

The transparent material should be flexible and moldable so that the panel may conform to the curvatures of a person's mouth. The transparent material should also emit most of the light from the electromagnetic radiation source to the teeth surface. One example of a suitable transparent materials is moldable, flexible plastic. Transparent panel 28 may be molded, embedded, or attached to the dental tray over light source panel 24. Transparent panel 28 may also protect the LEDs from damage. In addition, a clear resin 26 may be provided between transparent panel 28 and LEDs 22 to provide additional support and protection.

The light sources, such as LEDs 22, may be provided at some predetermined distance, for example, one LED per tooth, or may be provided relatively close together, such as illustrated in FIG. 1B. The particular spacing of LEDs 22 is determined and is chosen to optimize the desired whitening or cleaning activity provided by the electromagnetic radiation emitted from the LEDs.

FIG. 1D depicts a portion of dental tray 22 in which the dental tray includes a light source panel 24 covered by a transparent panel 28. The effectiveness and efficiency of the emitted electromagnetic radiation may be enhanced by adding a reflector, such as reflective panel 34, positioned against the non-illuminated side of light source panel 24 (e.g., FIGS. 1E to 1G). Any suitable reflector may be used including mirrors and foils. The reflector should be made of a material that causes most, if not all, of the light to be reflected back toward the tooth surface. FIG. 1F shows a portion of a dental tray having one transparent panel 28 over light source panel 24, and another transparent panel 28 positioned under reflective panel 34. This additional transparent panel may provide additional protection and structure to the light source panel. In FIG. 1G, a diffuser panel 32 is shown disposed between the light emitting side of light source panel 24 and transparent panel 28. Diffuser panel 32 acts to diffuse the light and provide a more uniform emission of light toward the tooth surface. In addition, diffuser panel 32 may be a polarizer causing a separation of wavelengths of light, especially in devices employing polychromatic light sources.

As shown in FIG. 2, when side-mounted LEDs are utilized, contacts 30 extend into light source panel 24. When surface-mounted LEDs are utilized (FIG. 3), contacts 30 are provided on the surface of light source panel 24.

FIG. 4A illustrates dental device 10, such as a dental tray 12, which includes electromagnetic radiation source 20. In the illustrated embodiment, electromagnetic radiation source 20 is internally disposed within dental tray 12. The illustrated embodiment also includes an optical fiber bundle 44 extending into electromagnetic radiation source 20. FIG. 4B illustrates a dental device 10 similar to the dental device of FIG. 4A, except that the electromagnetic radiation source is externally positioned with respect to dental tray 12. Accordingly, optical fiber bundle 44 is disposed between electromagnetic radiation source 20 and dental tray 12. Optical fiber bundle 44 acts to direct light from an energy source to one or more optical fibers, described herein.

The dental devices of FIGS. 4A and 4B utilize a light source panel 24 which comprises one or more layers of optical fibers 42 (FIGS. 4C and 4D) or fiber optic pipes. The optical fibers may be woven together. Multiple layers may provide more efficient use of the energy from the electromagnetic radiation source, and may enhance the brightness and uniformity of the light emitted from the light source panel to the target area (e.g., the dentifrice and teeth). The panel of woven optical fibers may be molded or embedded in the dental tray. In another example, light may be emitted from a single side of the panel with a relatively high intensity, and a reflective panel may be provided attached to the outer layer of woven optical fibers. Similar to the embodiment of FIG. 1, a diffuser panel may be provided to increase the uniformity of the light on the tooth surface. One example of a suitable optical fiber panel is the Lumitex®panel (Lumitex, Inc. Strongsville, Ohio, USA), as disclosed in U.S. Pat. No. 5,613,751, entitled LIGHT EMITTING PANEL ASSEMBLIES, the contents of which are hereby incorporated by reference.

FIG. 4E illustrates one device of the invention in which an optical fiber panel 42 is covered by transparent panel 28. FIG. 4F shows a similar device, but one that includes reflective panel 34. FIG. 4G shows a portion along box 4G of FIG. 4C in which diffuser panel 32 is disposed between transparent panel 28, and optical fiber panel 42. FIG. 4H is similar to FIG. 4G showing an additional transparent panel 28 below reflective panel 34. FIG. 4I is taken along the box 4I of FIG. 4D, illustrating a light source panel 24 below optical fiber panel 28.

In using the foregoing devices of the invention, a dentifrice, including, but not limited to pastes and gels, is placed in the dental tray, and the tray with the dentifrice is fit over the upper or lower teeth. The electromagnetic radiation sources are then activated, and the tray is kept in the mouth for a predetermined duration. The dentifrice will typically contain one or more active ingredients depending on the particular application. For example, the dentifrice may include one or more of the following compounds: peroxy compounds (such as, hydrogen peroxide and/or carbamide peroxide), oxidoreductase agents (such as laccases, oxidases, and/or peroxidases), antibacterial agents (such as chlorhexidine digluconate, hexetidine, alexidine, quarternary ammonium and water-soluble sources of certain metal ions such as zinc, copper, silver, and stannous), anti-carries agents (such as fluoride), anti-plaque agents or plaque control activators, anti-tartar agents, desensitizing agents, etching agents (such as phosphoric acid), photosensitizers and photodynamic therapy photosensitizers, whitening agents, or pigments. Peroxy compounds may be preferred for teeth-whitening applications. In certain embodiments, the dentifrice may be placed in the tooth bed of the dental tray.

The dental tray of the invention may also include one or more attachments to deliver the dentifrice from a cartridge 50 through a cartridge channel 52 directly into the tray (FIG. 5). The same attachment, or a different attachment, can be used for connecting an aspirator 60 to aspirate the dentifrice through aspirator channel 62 from the dental tray after the procedure is performed (FIG. 6).

In other embodiments of the invention, the dental trays may include a separate compartment to be aligned with a subject's gum line. Such a compartment may serve to contain an isolating gel that protects the gums from contact with the active ingredients of the dentifrice. The isolating gel may also include a thermal insulator that may help prevent heat transfer from the tray and/or the dentifrice to the gums. In addition, the dental tray could be structured to accept gel only on the side of the teeth requiring treatment, for example, the front side. The dental tray could include two or more sub-trays inside the main tray that provide selective treatment on different groups of teeth at the same time. For example, one sub-tray could be used for a fluoride treatment of the back molars, and another sub-tray could be used for whitening the front teeth. Thus, the device of the invention may include one or more compartments to customize the application of the device. The compartments may permit selective procedures to be performed on desired regions of the teeth or mouth, and/or may help protect sensitive areas of the mouth.

The dental tray may also be constructed to emit heat. This may be in addition to, or instead of, the electromagnetic radiation source. For example, a dry chemical heat-emitting material may be incorporated or added to the tray. The emission of heat may be activated after the user places the tray on his teeth and the user starts biting down on the tray. One example of a suitable chemical is sodium acetate trihydrate. In certain embodiments, the heat source is incorporated into the tray so that the subject wearing the dental tray does not ingest the heat source.

Figure 7A:
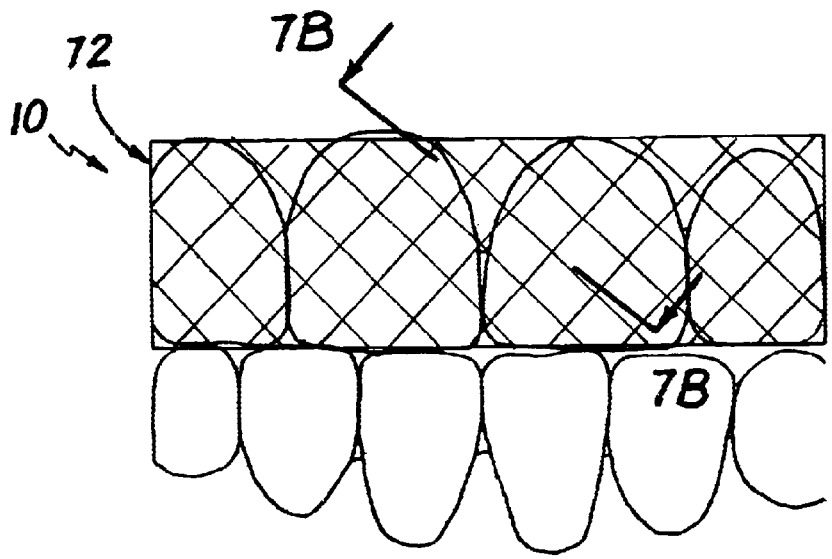
FIG. 7A is a side elevational view of the device of the invention in which the device is a dental band or dental tape disposed on teeth.
Figure 7B:
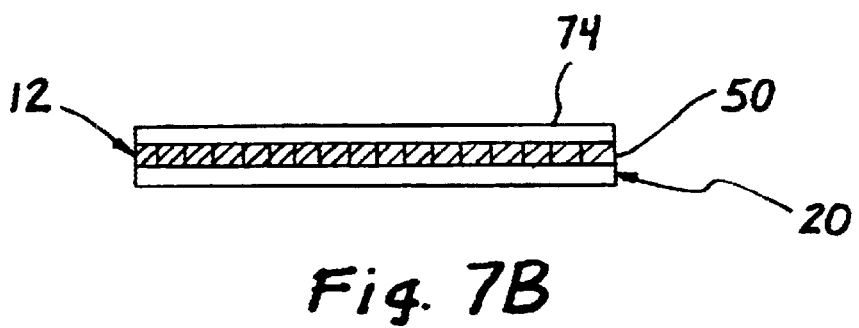
FIG. 7B is a sectional view along line 7B—7B of FIG. 7A.

FIG. 7A depicts dental device 10, such as a dental band or dental tape 72 attached to a person's teeth. In the illustrated embodiment, dental tape 72 is illustrated as a plurality of intersecting lines. The cross-section along line 7B—7B is shown in FIG. 7B. Dental tape 72 includes an electromagnetic radiation source 20. Dental tape 72 may also include one or more compartments 50 containing a dentifrice with an active ingredient sensitive to electromagnetic radiation. Each tooth of the subject may be covered by one or more of the compartments. A protective layer 74 may be provided over compartments 50 to prevent leakage of the dentifrice from the compartments. Protective layer 74 may be peeled off before applying the tape to the teeth. Alternatively, the protective layer may be made of a material subject to degradation by enzymes contained in a subject's mouth, where the enzymes dissolve the protective layer and thereby permit the dentifrice to be applied to the teeth. The electromagnetic radiation source may comprise a thin layer of woven optical fibers (e.g., Lumitrex), similar to that discussed above, a thin layer of LEDs, or even an organic or polymeric thin-film of luminescent material.

Examples of potential compounds or agents used in organic or polymeric thin-film luminescence include, but are not limited to, end-capped oligothiophenes, tris-chelated polypyridyl ruthenium (II) complexes, polyphenylenes, doped tris-8-(hydroxyquinoline) aluminum, indium tin oxides, polyfluorenes, vinylene-bridged triphenylamine dimers, rhodamine 6G, bicarbazyles, 1,1,4,4-tetraphenyl-1,3-butadiene-doped polymeric Langmuir-Blodgett films, inorganic CdSe nanocrystals, carbazole-substituted polyacetylenes The electromagnetic radiation source provided with the carrier in the dental device of the invention may be powered by any suitable means that can cause electromagnetic radiation to be emitted from the source or sources. For example, the dental tray electromagnetic radiation source may include one or more batteries, or an electrical power cord plugged into an electrical outlet. Batteries may be embedded in the tray or external to the tray. Dental tape may be provided with batteries placed within the tape, or may be able to be charged using a charging device.

The device of the invention may also include a programmable microprocessor, which may control parameters such as light, wavelength, brightness, power, or duration of emission. The parameters may be programmed as presets, or may be operated manually by the user. For example, the user may control the speed of whitening by selecting the wavelength, the brightness, the power, and the time of exposure. For in-office procedures, a clinician may decide the specific parameters suited for the patient. For out of office procedures, such as home use, the user may select one of the preset programs. For example, a program providing a higher light intensity for a relatively short duration. In addition, the dental device may include a sensor device that, through software control, would let the user know when the process is completed or the treatment time has expired.

Thus, the dental device of the invention is easy to use, and may provide fast and effective treatment over conventional devices. The dental device of the invention may provide selective treatment for specific tooth surfaces, and better alignment and a more controlled, uniform treatment. The device may reduce tooth sensitivity. The device may require less time for wearing the device, and may reduce discomfort associated with whitening agents contacting the teeth for a long period of time. The device provides means for treating teeth or portion of teeth locally. The clinician is not required to point the electromagnetic radiation source to every tooth, as is conventionally done.

While this invention has been described with respect to various specific examples and embodiments, it is to be understood that the invention is not limited thereto and that it can be variously practiced with the scope of the following claims.

What is claimed is:

1. A dental device for exposing teeth to electromagnetic radiation comprising:
    a carrier constructed to be applied to at least one tooth; and
    at least one light source attached to the carrier and oriented to emit electromagnetic radiation from the light source toward a tooth surface.

2. The dental device of claim 1, further comprising a power supply operably connected to the at least one light source, the power supply providing energy to the light source.

3. The dental device of claim 1, wherein the at least one light source is a light emitting diode.

4. The dental device of claim 1, wherein the light source is an optical fiber panel.

5. The dental device of claim 1, wherein the light source is an electrochemiluminescent material.

6. The dental device of claim 1, further comprising an optical fiber bundle operably connected with the light source so that optical energy may be transmitted from the optical fiber bundle to the light source.

7. The dental device of claim 1, further comprising a circuit for varying at least one of an intensity, distribution and duration of electromagnetic radiation emitted from the light source.

8. The dental device of claim 1, further comprising a transparent panel disposed over the light source.

9. The dental device of claim 1, further comprising a reflective panel disposed between the light source and the carrier.

10. The dental device of claim 1, further comprising a diffuser panel disposed over the light source.

11. The dental device of claim 1, wherein the light source comprises a layer of woven optical fibers.

12. The dental device of claim 1, further comprising at least one compartment located on or within the dental tape, the at least one compartment constructed to contain a dentrifice with an active ingredient sensitive to electromagnetic radiation.

13. The dental device of claim 12, wherein the at least one compartment is located at a surface of the dental tape that is disposed between the light source and the subject's teeth when the dental tape is attached thereto.

14. A dental device for exposing teeth of a subject to electromagnetic radiation, comprising:

a dental tray structured to fit over teeth of the subject; and at least one optical fiber configured to provide electromagnetic radiation to at least one tooth, the at least one optical fiber being disposed on or within the dental tray so that the electromagnetic radiation is directed toward at least one tooth of the subject.

15. The dental device of claim 14, wherein the at least one optical fiber comprises a plurality of optical fibers defining an optical fiber panel.

16. The dental device of claim 14, the at least one optical fiber comprising a plurality of optical fibers and the dental device further comprising a power source in communication with the plurality of optical fibers, the power source providing power to the plurality of optical fibers.

17. The dental device of claim 14, the at least one optical fiber comprising a plurality of optical fibers and the dental device further comprising a circuit for varying at least one of an intensity, distribution and duration of electromagnetic radiation emitted from the plurality of optical fibers.

18. The dental device of claim 14, further comprising a reflective panel disposed between the at least one optical fiber and the dental tray.

19. The dental device of claim 14, further comprising a diffuser panel disposed over the at least one optical fiber.

20. A method for exposing teeth to electromagnetic radiation, the method comprising the following steps:

(a) providing a dental device, which comprises a carrier and at least one optical fiber disposed on or within the carrier;

(b) applying a dentifrice;

(c) applying the dental device to a subject's teeth; and (d) activating a source of electromagnetic energy so that electromagnetic radiation is emitted from the at least one optical fiber in a direction toward the dentrifice.

21. The method of claim 20, wherein:

the step of applying a dentifrice comprises a step of applying a dentifrice containing an agent having at least one of cleaning, sterilizing and whitening properties; and the step of activating a source of electromagnetic energy comprises a step of activating a source of electromagnetic energy so that electromagnetic radiation is emitted from the at least one optical fiber in a direction toward the subject's teeth.

22. The method of claim 21, and further comprising a step of the agent being at least partially activated by the electromagnetic radiation emitted from the at least one optical fiber.

23. The method of claim 20, wherein the step of applying a dentifrice comprises a step of applying a dentifrice to the dental device.

24. The method of claim 20, wherein the step of applying a dentifrice comprises a step of applying a dentifrice to a subject's teeth.

25. The method of claim 20, wherein the at least one optical fiber comprises a plurality of optical fibers.

26. The method of claim 20, wherein the dentifrice comprises a peroxy compound and a fluoride.

27. The method of claim 20, wherein the dentifrice comprises an anti-carries agent.

28. The method of claim 20, wherein the dentifrice comprises a peroxy compound, an oxidoreductase agent, an antibacterial agent, an anti-carries agent, an anti-plaque agent or plaque control activator, an anti-tartar agent, a desensitizing agent, an etching agent, a photosensitizer or photodynamic therapy photosensitizer, and a whitening agent.

* * * * *

UNITED STATES PATENT AND TRADEMARK OFFICE
CERTIFICATE OF CORRECTION

PATENT NO. : 6,616,447 B1
DATED : September 9, 2003
INVENTOR(S) : Rizoiu et al.

It is certified that error appears in the above-identified patent and that said Letters Patent is hereby corrected as shown below:

Column 4,
Line 25, "a preferred embociment," should read -- a preferred embodiment, --

Column 8,
Line 59, "a carrier constructed to be applied to" should read -- a dental tape constructed to be applied and attached to --
Line 61, "to the carrier and" should read -- to the dental tape and --

Column 9,
Line 17, "claim 1, further comprising a" should read -- claim 1, wherein the light source includes a non-illuminated side, and the dental device further comprises a --
Line 19, "carrier." should read -- carrier, so that the reflective panel is positioned against the non-illuminated side of the light source. --
Line 27, "dentrifice with an" should read -- dentifrice with an --
Line 35, "a dental tray structured to fit over teeth of" should read -- dental tape structured to fit over and attached to teeth of --
Line 38, "the dental tray" should read -- the dental tape --

Column 10,
Line 3, "claim 14, further comprising a" should read -- claim 14, wherein the at least one optical fiber includes a non-iluminated side, and the dental device further comprising comprises a --
Line 5, "the dental tray." should read -- the dental tray, so that the reflective panel is positioned against the non-illuminated side of the at least one optical fiber. --
Lines 10-11, "a carrier and" should read -- a dental tape constructed to be applied and attached to at least one tooth of a patient, and --

UNITED STATES PATENT AND TRADEMARK OFFICE
CERTIFICATE OF CORRECTION

PATENT NO. : 6,616,447 B1
DATED : September 9, 2003
INVENTOR(S) : Rizoiu et al.

It is certified that error appears in the above-identified patent and that said Letters Patent is hereby corrected as shown below:

Column 10, cont'd.,
Lines 11-12, "within the carrier;" should read -- within the dental tape; --
Line 17, "toward the dentrifice" should read -- toward the dentifice --

Signed and Sealed this

Thirty-first Day of August, 2004

JON W. DUDAS
*Director of the United States Patent and Trademark Office*